United States Patent [19]
Fidler et al.

[11] Patent Number: 5,198,771
[45] Date of Patent: Mar. 30, 1993

[54] POTENTIOSTATIC APPARATUS AND METHODS

[75] Inventors: John C. Fidler, DeKalb; James P. Bobis, Downers Grove; William R. Penrose; Joseph R. Stetter, both of Naperville, all of Ill.

[73] Assignee: Transducer Research, Inc., Naperville, Ill.

[21] Appl. No.: 753,835

[22] Filed: Sep. 3, 1991

[51] Int. Cl.$^5$ .............................................. G05F 1/46
[52] U.S. Cl. .................................... 324/438; 324/444; 204/406; 204/231
[58] Field of Search ................... 204/406, 407, 153.10; 324/438, 444

[56] References Cited
U.S. PATENT DOCUMENTS 4,227,988 10/1980 Galwey ................................. 204/406
4,230,554 10/1980 Blanke ................................. 204/406
4,348,632 9/1982 Galwey ................................. 204/231
4,459,180 7/1984 Fogel ................................... 204/406
4,498,039 2/1985 Galwey ................................. 204/406

Primary Examiner—Kenneth A. Wieder
Assistant Examiner—Jose M. Solis

[57] ABSTRACT

A potentiostat for an amperometric sensor uses a voltage-controlled current source (VCCS), which may be either unidirectional or, preferably, bidirectional. An error amplifier compares the potential of the sensor's reference or counter electrode, relative to ground potential, to a set-point potential. The error voltage serves as an input to the VCCS. The output of the VCCS—a current proportional to the error voltage—is supplied to the sensor's auxiliary electrode. In a steady state, the error voltage is just large enough to supply current that is equal to the current through the sensor's working and auxiliary (or counter) electrodes. The error voltage can either serve directly as an output voltage or it can be amplified without introducing a feed-back loop disturbance. The VCCS permits direct grounding of the sensor's working electrode and operation of the error amplifier at a low or moderate gain, so as to increase the circuit's frequency response and reduce the probability of oscillation. Also, in conjunction with an adjustable low-pass filter, the VCCS permits optimization of the system's frequency response so as to yield improved stability.

3 Claims, 3 Drawing Sheets

BACKGROUND CURRENT: 1.7μA
STEADY STATE CURRENT: 65μA
200 ppm CO CURRENT: 63.4μA

BACKGROUND CURRENT: -2.2μA
STEADY STATE CURRENT: 65.3μA
200 ppm CO CURRENT: 67.5μA

POTENTIOSTATIC APPARATUS AND METHODS

BACKGROUND OF THE INVENTION

This invention relates to apparatus and methods for controlling and maintaining a stable difference in electrical potential between two selected elements of an electrochemical device. Electrical circuits for achieving such a controllable and stable potential are called potentiostats, and are most commonly used with amperometric devices for measuring the concentrations of specific substances in the gas or liquid phase. A second function of the potentiostat is to provide an output signal that is representative of the quantity of the substance being analyzed. The amperometric device and the potentiostat together form a chemical measuring system; both components are essential to the measuring operation.

Amperometric gas sensors often use sensing, or working, electrodes made of finely divided catalyst material, which has a large surface area per unit weight. The electrical capacitances of these electrodes are very large. With conventional potentiostat circuits, the sensor-potentiostat system often becomes unstable and oscillates. It is the object of this invention to provide a potentiostat circuit whose stability is not affected by large capacitances in the sensor.

An amperometric sensor consists of either two or three electrodes immersed in an ionically conducting medium, which is usually an electrolyte solution. In the three-electrode version, the electrodes are named the working electrode, the reference electrode, and the auxiliary electrode. The working electrode is the site of the analytical reaction; in a gas sensor, it is exposed to the sample of the gas being monitored. The reference electrode is designed to be at a constant electrical potential relative to the electrolyte solution. In the three-electrode version, it is important to the functioning of the reference electrode that no current flows in it. In such cases, the auxiliary electrode is used to provide an electrical current to the electrolyte solution that is equal and opposite in sign to the current at the working electrode.

In a two-electrode sensor, a current may flow through the reference electrode, and the functions of the reference electrode and auxiliary electrode are combined in one electrode. This is called the counter electrode.

A potentiostat circuit always contains a feedback loop, in which the potential of the reference (or counter) electrode is measured relative to the working electrode. This measured potential (cell potential) is combined with a desired potential (the set-point potential) to obtain an error signal in the form of a voltage. In the potentiostat circuits that are conventionally used with amperometric sensors, the error voltage is applied directly to the auxiliary (or counter) electrode, causing a current to flow. When the system is at equilibrium, the reference potential relative to the working electrode is equal in magnitude to the set-point potential.

Such circuits provide a way of controlling the operation of the sensor, but do not provide a way of obtaining an output signal. To obtain an output signal, the feedback loop must be compromised in one of two ways. In one way, the working electrode is connected to a current-to-voltage converter circuit. At equilibrium, this circuit forces the working electrode to maintain a potential near ground potential. The reference (or counter) electrode voltage is therefore measured relative to ground. Because the response time of existing operational amplifiers is not infinitely fast, the voltage of the working electrode will deviate from ground when the current flow changes at a rapid rate. This results in an erroneous measurement of the cell potential which causes a fluctuation in the voltage applied to the counter electrode. The result may be a high-frequency oscillation, which is rendered more likely by large electrode capacitances. In addition, noise may be increased if a long cable is connected between the sensor and the potentiostat.

The second way of obtaining an output signal is to insert a current-sensing resistor in series with the auxiliary or counter electrode. The voltage across the sensing resistor is directly proportional to the magnitude of the current flowing through the counter electrode. A differential amplifier is connected across the sensing resistor and the output of the differential amplifier becomes the output signal. The problem with this method is that a large value of resistance must be used to provide a measurable signal. A large sensing resistor could limit the voltage available to drive the counter electrode for maintaining a constant potential relative to the electrolyte solution. If a smaller sensing resistor is used, the gain of the differential amplifier must be increased to accommodate the smaller voltage across the sensing resistor. Additional gain in the differential amplifier can introduce error signals due to common mode rejection, impedance loading of the sensor, and increased noise signal or else increase significantly in the number of operational amplifiers needed for the electrical circuit.

It is object of this invention to provide a potentiostat circuit in which the working electrode of the sensor is connected directly to ground, so as to improve the sensor's signal-to-noise ratio.

It is another objective of this invention to provide a potentiostat circuit for an amperometric sensor with a directly grounded working electrode that permits measurement of very small currents typically generated in amperometric gas sensors without resorting to a high-gain differential amplifier.

It is still another object of this invention to provide a potentiostat circuit that will operate in a stable manner with an amperometric sensor whose working electrode has a high capacitance.

It is yet another object of this invention to provide an amperometric sensor with a potentiostat circuit that allows the operating parameters of the feedback loop to be controlled apart of the operating parameters of the circuit that generates the output signal. For example, the frequency response of the feedback loop of the invention may be deliberately controlled without affecting the design of the circuit for generating the output signal.

SUMMARY OF THE INVENTION

Briefly, the invention consists of a potentiostat for an amperometric sensor using a voltage-controlled current source (VCCS). The current source may be unidirectional or bidirectional, although the latter is preferred. A differential amplifier compares the potential of the reference (or counter) electrode, measured relative to ground potential, to the desired, or set-point, potential. The error voltage is used as an input to the VCCS. The output of the VCCS—a current proportional to the error voltage—is supplied to the auxiliary electrode.

When the system is in a steady state, the error voltage is just large enough to yield a current that is equal to the current through the working electrode and the auxiliary (or counter) electrode. The error voltage can also be used as an output voltage. If the output voltage must be scaled to fit a particular application, the voltage may be amplified by any desired amount without disturbing the feedback loop.

The use of the VCCS to control the potential of the reference electrode permits direct grounding of the working electrode. It also permits operation of the error amplifier at a low or moderate gain, thereby increasing the frequency response of the system and reducing the probability of oscillation. Also, in conjunction with an adjustable low-pass filter, the VCCS permits optimization of the system's frequency response so as to yield improved stability.

BRIEF DESCRIPTION OF THE DRAWINGS

The invention is best explained with reference to the drawings, in which.

DESCRIPTION OF THE PREFERRED EMBODIMENT

Figure 1:
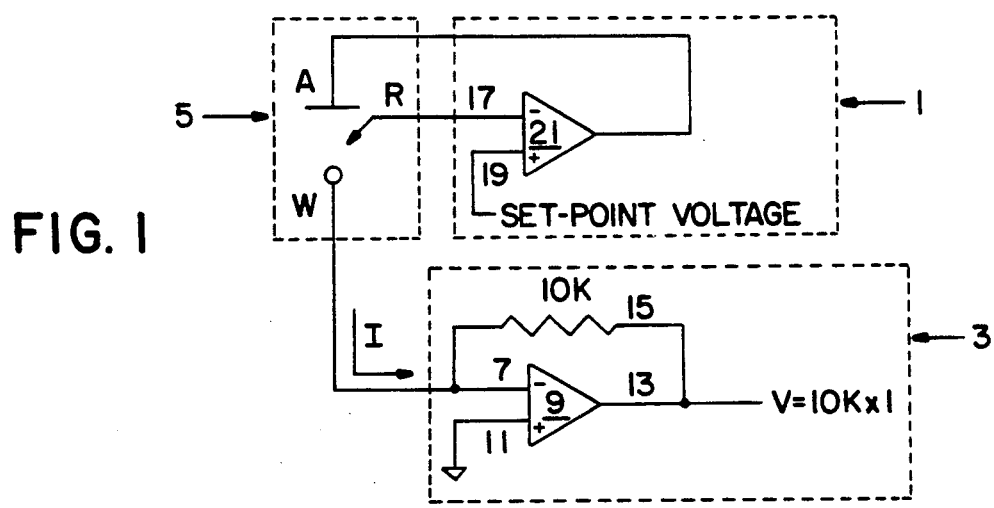
FIG. 1 is a circuit diagram of a conventional potentiostat circuit.

The preferred embodiment may be understood by comparison with the conventional potentiostat of FIG. 1. In its simplest form, the conventional potentiostat consists of two sections—an error amplifier 1 and a current-to-voltage converter 3. Also shown in FIG. 1 is a representation of the sensor 5. The reaction of the analyte, i.e., chemical being monitored, occurs at the working electrode W. This reaction either supplies or removes electrons to or from the working electrode, depending on the reaction. A current I flows from W to the inverting input 7 of the operational amplifier 9. This causes the voltage at input 7 to rise or fall. The non-inverting input 11 is held at ground potential, so that the output 13 of the operational amplifier generates a positive or negative voltage V. The voltage V causes a current to flow through the resistor 15 to the inverting input of the operational amplifier. When the circuit is in a steady state, the current flowing from output 13 through resistor 15 is equal and opposite to the current flowing from the working electrode. In principle, no current flows in or out of the inputs of an operational amplifier. Thus, no charge accumulates on the inverting input and its voltage is close to ground. Any change in current from the working electrode causes the output voltage to change and force a new current through the resistor until it is equal to the working electrode current. Therefore the output voltage is proportional to the input current. Meanwhile, the working electrode W is kept very close to ground potential, although it is not connected to ground. This is called a virtual ground.

The reference electrode R has a potential that is related to the characteristics of the electrode itself, as well as the electrical potential of the solution. Since reference electrodes are designed to be as stable as possible, a constant potential difference between R and W assures stable operation of the working electrode. The reference electrode R is connected to the inverting input 17 of the differential amplifier 21. To the non-inverting input 19 is n connected a desired set-point voltage, to which the measured reference electrode will be compared. The difference in the two voltages generates a change in the voltage output of the operational amplifier 21 which causes a current to flow to or from the auxiliary electrode A. At steady state, the current through the auxiliary electrode equals that through the working electrode. A change in current at the working electrode, due to a change in the reaction of the chemical being monitored, causes a net electrical charge to develop in sensor 5. This causes the reference potential and the output voltage of the operational amplifier to change until the current through the auxiliary electrode again equals that through the working electrode.

The difference potential between the differential inputs of the operational amplifier 21 will increase for higher frequencies due to the frequency response of the amplifier. This will cause the working electrode potential to move farther from ground, increasing the error in working electrode potential relative to the reference electrode potential. With the working electrode potential no longer at ground, the system may become unstable. This instability can be avoided with the embodiment of the invention that is represented by the block diagram of FIG. 2. The VCCS potentiostat comprises an error amplifier 31, a voltage-controlled current source 33, and an optional filter. In this circuit, the working electrode W of sensor 35 can be grounded, eliminating a major source of instability. The voltage of the reference (or counter) electrode R is compared to the desired, or set-point, voltage by the error amplifier 31, as in the conventional potentiostat of FIG. 1. The error voltage, however, is not connected directly to the auxiliary (or counter) electrode. It is connected instead, either directly or through intermediate circuit elements, to the input 37 of the VCCS 33. The output 41 of the VCCS is connected to the auxiliary (or counter) electrode A.

In a preferred embodiment of the invention, the VCCS potentiostat is used to set the reference voltage of the sensor equal to the set-point voltage. The set-point voltage is compared by the error amplifier to the potential at the reference lead of the sensor. The output of the error amplifier, which can be measured at an output voltage terminal (not shown), is applied to a filter circuit that conditions the signal and is then summed with an offset voltage and applied to the voltage-controlled current source. The offset voltage shifts the voltage at the output of the error amplifier to the value that is required to maintain the proper potential at the reference lead of the sensor. The current $I_S$ from the VCCS is applied to the source lead of the sensor so as to maintain the set reference potential of the sensor relative to the ground potential.

Figure 2:
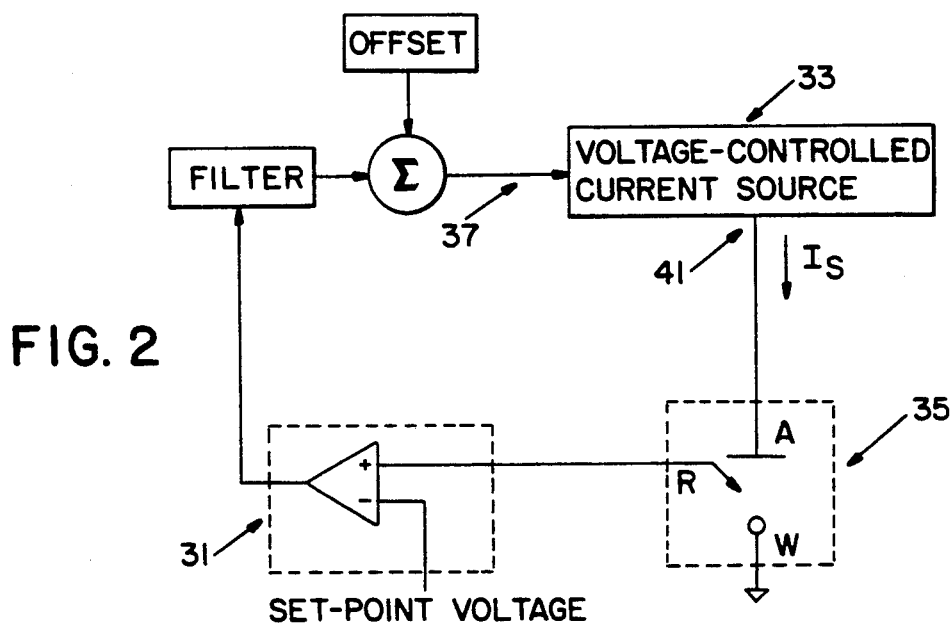
FIG. 2 is a block diagram of the potentiostat circuit of the present invention.
Figure 3:
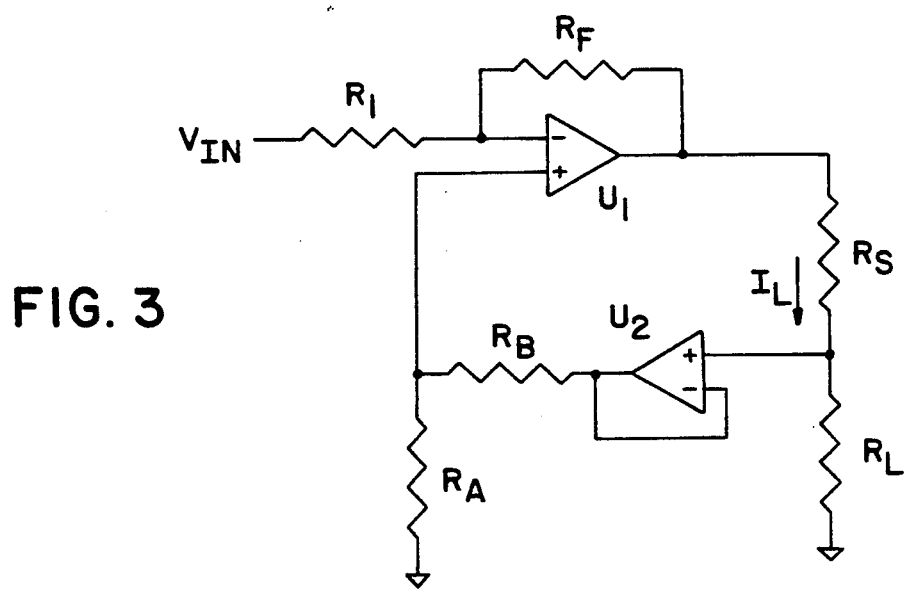
FIG. 3 is a circuit diagram of a voltage-controlled current source.

The VCCS 33 of FIG. 2 may be represented by the circuit diagram of FIG. 3. The modified Howland current pump can be used as the VCCS. The operational amplifier $U_1$ is used as the main amplifier for the VCCS. Resistor $R_S$ is used to determine the amount of current $I_L$, that is flowing out of the pump for any given voltage input, $V_{IN}$. Resistors $R_1$ and $R_F$ combined with $R_S$ determine the transfer conductance of the VCCS. The output current becomes:

$$I_L = \frac{V_{IN}R_F}{R_1 R_s}$$

To maintain a stable voltage across $R_S$ for varying load resistances, positive feedback is provided by $R_B$ and $R_A$. If the voltage across the load oscillates, the positive feedback changes the output voltage of $U_1$ so that the voltage across $R_S$ remains stable. The ratio of $R_B + R_S$ to $R_A$ is equal to the ratio of $R_F$ to $R_1$ in this circuit. The stable voltage across $R_S$ establishes a stable output current for a given input voltage. The second operational amplifier, $U_2$, is a unity-gain follower used to provide a high impedance to $R_L$ so that the load current only flows into the sensor that is represented in FIG. 3 by $R_L$.

It is implicit in the above descriptions that, in two-electrode sensors, the electrodes A and R form a single counter electrode which is both the source of the feedback signal (the electrode potential) and the destination of the feedback signal (the current output).

Normally, the frequency response (or bandwidth) of an op amp (operational amplifier) is inversely proportional to the gain for which the op amp is used. The characteristic parameter is called the gain-bandwidth product. When the error amplifier is used at maximum gain, as in the conventional potentiostat, the frequency response is very low. Combined with the high working electrode capacitance of certain gas sensors, this may produce sufficient phase shift between working electrode current and error voltage to result in oscillation of the system. When a VCCS is used to generate the current in the auxiliary (or counter) electrode, the error amplifier need not be operated at high gain. The frequency response of the system is therefore increased, and the likelihood of oscillation is reduced.

It is often preferable to reduce the frequency response of the sensor-potentiostat system to increase stability and reduce noise. This can be done by inserting a low-pass filter between the VCCS and the differential amplifier that compares the reference voltage with the set-point potential. This filter can be adjusted to optimize the frequency response of the system and improve stability.

The effectiveness of the VCCS circuit is demonstrated in the following examples:

EXAMPLE 1

Figure 4A:
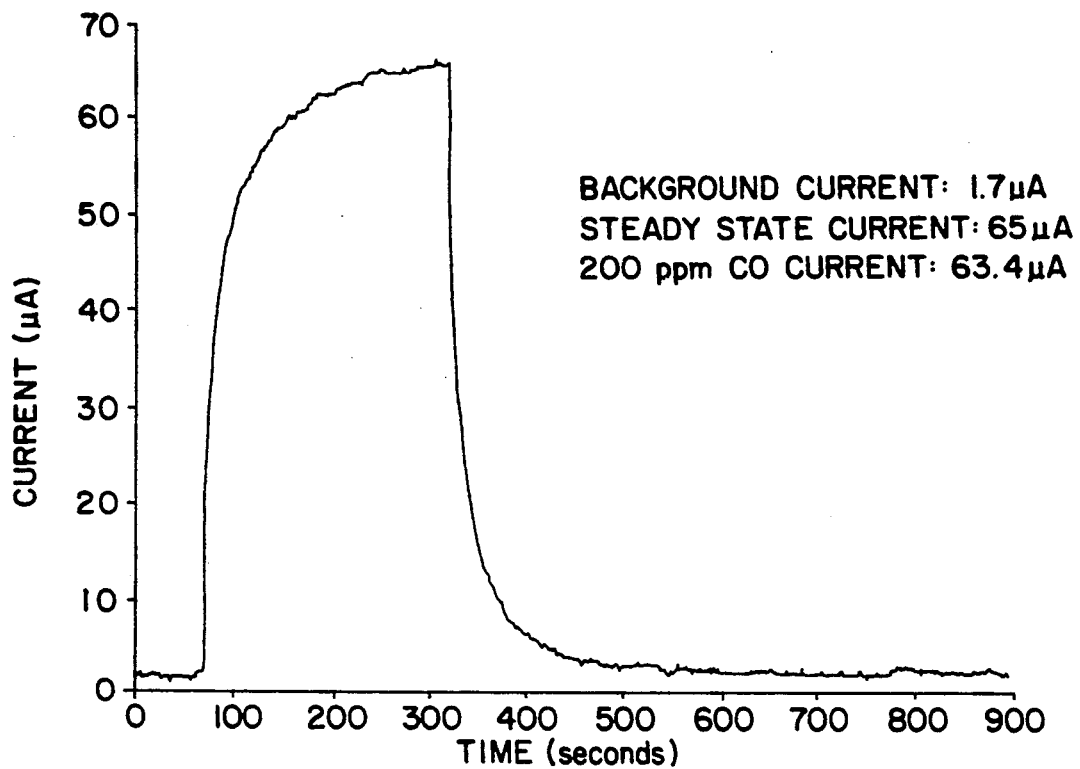
FIGS. 4A and 4B show a comparison of the response curves of one amperometric sensor that were obtained with the potentiostat circuits of FIGS. 1 and 2.
Figure 4B:
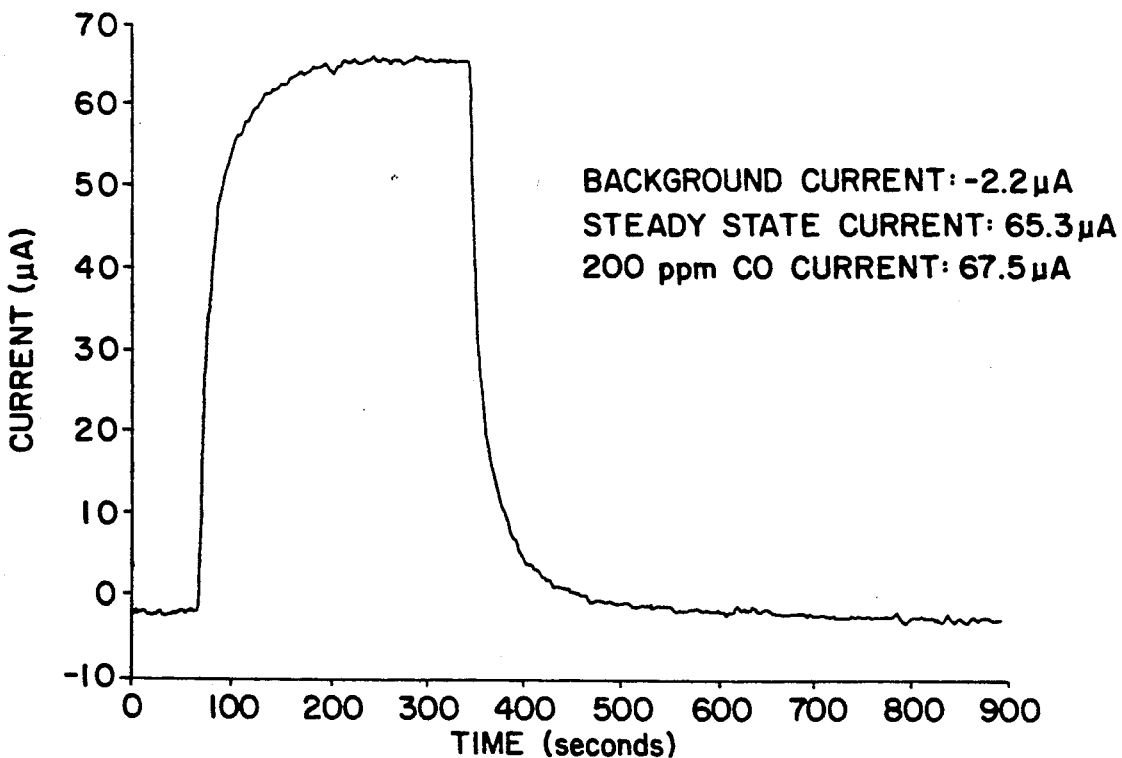

Circuits of the conventional and VCCS potentiostats were constructed. A comparison of the response to 200 ppm (parts per million) of CO was made on both circuits using the same amperometric gas sensor (a Transducer Research Inc. Model ECS-3330-D Carbon Monoxide Sensor). The test was begun with one minute of background measurement (no gas) to determine the baseline current and four minutes of exposure to CO to determine the sensor response to a steady-state flow of the analyte vapor. Following exposure, the recovery of the sensor was monitored for ten minutes. The data for both potentiostatic systems were taken using a datalogger with a sample interval of one second. The output from the current follower used in the conventional potentiostat was passed through a 1-Hz low-pass filter before being applied to the datalogger. The response of the conventional potentiostatic system is shown in FIG. 4A. Since output from the VCCS potentiostatic system did not include a 1-Hz filter, the data are conditioned using a five-point moving average, which approximates the exponentially weighted averaging of a low-pass filter. The results from the VCCS potentiostatic system is given in FIG. 4B.

EXAMPLE 2

Figure 5A:
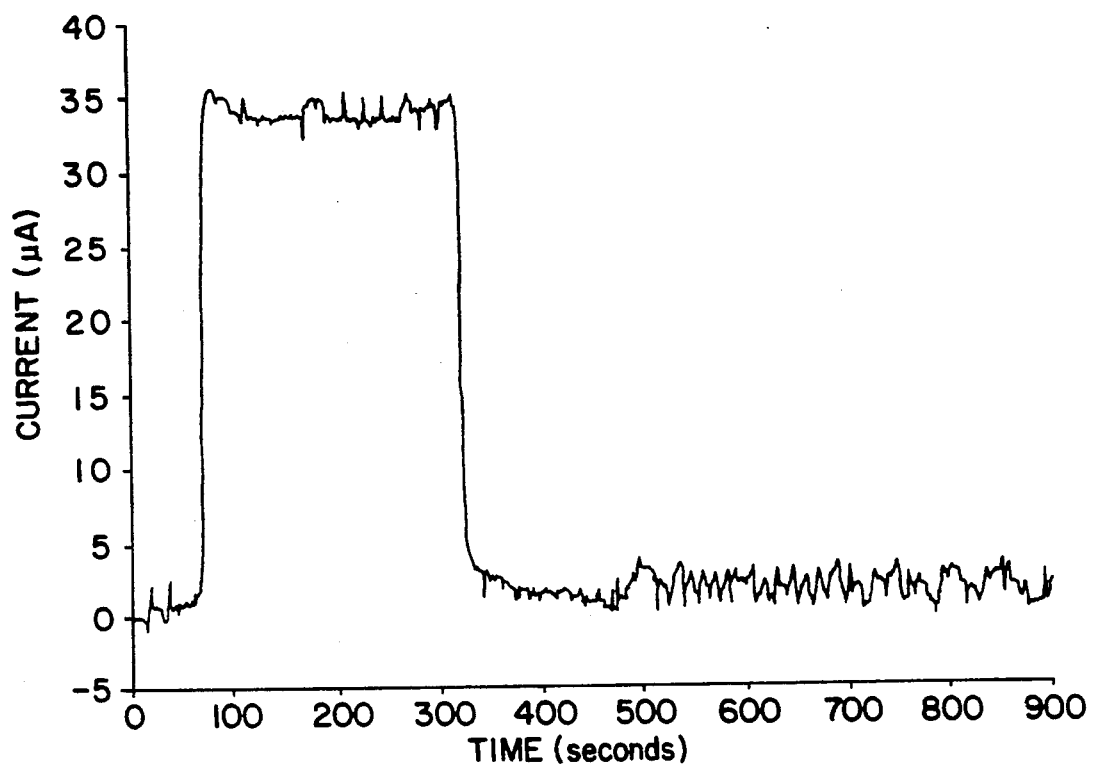
FIGS. 5A and 5B show a similar comparison of the response curves of an amperometric sensor of a different type.
Figure 5B:
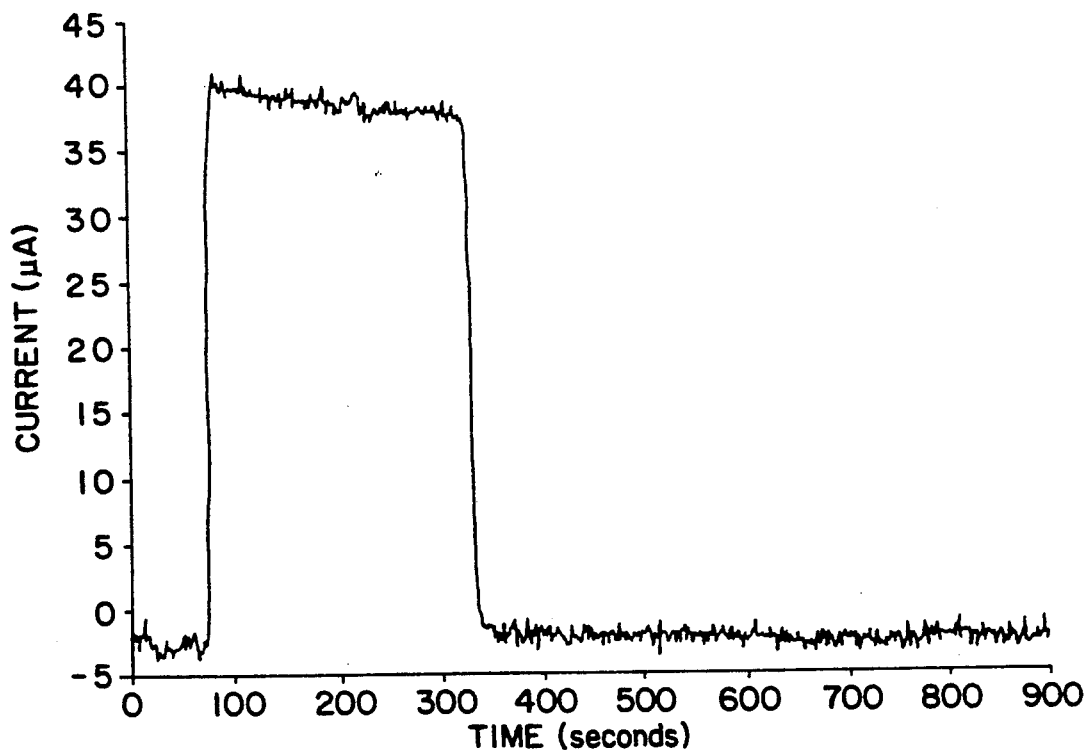

A second test was performed to determine how the VCCS potentiostat would behave using a sensor of an alternative design. Instead of an acid electrolyte, the second sensor is fabricated with Nafion, an ionically-conducting solid polymer. The response of this sensor is comparable to that of the sensor of Example 1, but unstable static performance in some of the Nafion sensors is observed using the conventional potentiostat, as shown in FIG. 5A. The instability is found to disappear when using a VCCS potentiostat, as shown in FIG. 5B.

A comparison of the data taken for the two different potentiostatic systems show that the VCCS potentiostat provides similar results to those generated by the conventional potentiostat. The test results show that the VCCS is a viable alternative to the standard potentiostat with the advantage of allowing the working electrode to be connected directly to the system ground. This improves overall system stability, as shown when using a sensor that was unstable with the conventional potentiostat design.

There will now be obvious to those skilled in the art many variations of the above-described embodiment which, however, shall remain within the scope of the invention if defined by the following claims.

We claim:

1. A potentiostat circuit for controlling and maintaining a stable potential difference between the working electrode and the reference or counter electrode of an amperometric sensor and for generating an output signal that is substantially proportional to the current flowing through said working electrode, said circuit comprising a voltage-controlled current source whose input is an error voltage generated by an error amplifier and whose output is a current that is proportional to the error voltage, wherein said error amplifier compares the potential of the reference or counter electrode, measured relative to ground potential, to a set-point potential, and wherein the error voltage gives rise to a current that is equal to the current passing through said working electrode when the current flow in said circuit is in a steady state, and wherein the voltage-controlled current source is a variant of the Howland current pump.

2. The circuit of claim 1, wherein said current pump comprises two operational amplifiers, one of which acts as the main amplifier for the voltage-controlled current source whereas the other amplifier is a high-impedance unity-gain follower.

3. The circuit of claim 2, comprising two resistors that provide a positive feedback which maintains a stable output current for varying load resistances.

* * * * *